United States Patent [19]

Feder et al.

[11] 4,201,845
[45] May 6, 1980

[54] CELL CULTURE REACTOR

[75] Inventors: Joseph Feder, University City, Mo.; Katharine Ku, San Francisco, Calif.; Mau-Jung Ku, Creve Coeur, Mo.

[73] Assignee: Monsanto Company, St. Louis, Mo.

[21] Appl. No.: 875,464

[22] Filed: Feb. 6, 1978

Related U.S. Application Data

[63] Continuation-in-part of Ser. No. 676,100, Apr. 12, 1976, Pat. No. 4,087,327.

[51] Int. Cl.² .......................... C12K 9/00; C12B 1/10
[52] U.S. Cl. ................................................... 435/285
[58] Field of Search ................ 195/127, 139, 1.7, 1.8; 210/23, 321, 500 M

[56] References Cited

U.S. PATENT DOCUMENTS

| | | | |
|---|---|---|---|
| 3,342,729 | 9/1967 | Strand | 210/23 |
| 3,746,175 | 7/1973 | Markley | 210/321 |
| 3,821,087 | 6/1974 | Knazek et al. | 195/127 |
| 3,843,454 | 10/1974 | Weiss | 195/127 |
| 3,883,393 | 5/1975 | Knazek et al. | 195/1.8 |
| 3,997,396 | 12/1976 | Delente | 195/1.8 |

OTHER PUBLICATIONS

Williams, et al., "A Hollow Filament Fabric Blood Oxygenator," Chp. 31, *Proceedings of the Artificial Heart Conference*, Heggeli ed., National Heart Institute, N.I.H., Bethesda, (1969), pp. 365-371.
Schratter, "Synthetic Capillaries for Cell Culture," *American Laboratory*, vol. 6, No. 10, (1974), pp. 33-38.
*Bulletin of Amicon Corporation*, "Membrane Perfusion by Artificial Capillaries," (1975), Lexington, Mass.

*Primary Examiner*—Thomas G. Wiseman
*Attorney, Agent, or Firm*—Scott J. Meyer; James W. Williams, Jr.

[57] ABSTRACT

A cell culture reactor is provided for the growth of cells in vitro which employs elongate, selectively permeable hollow fibers arranged in a shallow layer configuration as a matrix for cell attachment on the outer surface of the fibers, and aeration of the cells by passage through the interior of said fibers and permeation of the membrane cell. The flow path of the culture media is directed by distributor plate means substantially uniformly through the fiber layer and substantially transverse to the plane of the elongate axes of the fibers.

10 Claims, 7 Drawing Figures

CELL CULTURE REACTOR

Related Application

This is a continuation-in-part of copending application Ser. No. 676,100, filed Apr. 12, 1976, now U.S. Pat. No. 4,087,327.

Background of the Invention

This invention relates to apparatus for the culturing of cells.

The culturing of living cells in vitro is desired for a variety of purposes such as the preparation of viral vaccines, the recovery of valuable by-products of the cell metabolism and the production of tissue-like densities for creating artificial organs.

Various procedures have been developed previously for the culturing of anchorage dependent cells in vitro. One widely used method involves attaching and growing the cells on the interior surface of glass or plastic roller tubes and bottles. This method is exemplified by use of the Flow tube (Flow Laboratories) disclosed in U.S. Pat. No. 3,450,598. Another procedure used heretofore attaches and grows the cells on the flat side of appropriately shaped stationary containers such as, for example, the ordinary petri dish or rectangular shaped culture plates. The flat surface method also has been employed in apparatus having a stack of space-apart plates such as shown in U.S. Pat. No. 3,407,120; or apparatus having a continuous plastic sheet arranged around a set of spaced-apart supports as illustrated in U.S. Pat. No. 3,843,454; or apparatus having spiral tubing disposed around spacer members as seen from U.S. Pat. No. 3,948,732. Instead of using bare glass or plastic as the support surface for growing cells as monolayers, collagen-coated glass also has been employed. In order to provide a 3-dimensional support matrix for cell culturing, use of a collagen-coated cellulose sponge has been suggested heretofore.

Further background information on these and other such conventional cell culturing methods can be had by reference to a standard text in the field such as Kruse and Patterson, "Tissue Culture Methods and Applications", Academic Press, New York, 1973.

Recently, the use of hollow fibers or synthetic capillaries has been disclosed as a support matrix for the propagation of cells. This use was reported by Knazek, *Science* 178, 65-67 (1972), and specific apparatus for this cell culturing method is described in U.S. Pat. Nos. 3,821,087 and 3,883,393. The apparatus comprises a bundle of ultra-filtration fibers retained in a cylindrical shell or cartridge. In essence, the apparatus employs membrane perfusion by artificial capillaries. The extensive surface area of the hollow fiber system allows selective transport through the fiber walls and facilitates molecular exchange between the stream flowing through the fiber interiors and a liquid which bathes the outer surface of the fibers by a simple gradient diffusion. This hollow fiber apparatus is further described by Knazek in *Federation Proc.* 33, 1978-81 (1974), and in *Exptl. Cell Res.* 84. 251-4 (1974) wherein it is reported to produce HCG hormone from human choriocarcinoma cells at a rate eleven times higher than that grown on 75 cm$^2$ monolayer flasks (Falcon). Cartridge apparatus of the type disclosed by Knazek is commercially available from Amicon Corporation and its use in cell culturing is described in *American Lab.* October 1974, pp. 33-38.

Notwithstanding the usefulness of the Knazek apparatus and method, it has been found in practice that employment of the bundle or cartridge configuration with fluid flow of culture medium through the elongate capillary membranes prevents complete penetration of the fiber bundle by the cells and sets up an undesirable gradient of medium flow. The inability of the cells to fully penetrate the fiber bundle results in uneven dispersion of the cells and incomplete utilization of the available fiber surface for cell attachment. The undesirable gradient consists of an uneven distribution and utilization of liquid culture medium. As the medium flows through the reactor, nutrients are more available to the cells near the inlet, and as the medium flows to the outlet, metabolic products such as lactic acid accumulate in the medium, thereby undesirably affecting pH and producing other toxic effects on the cells.

Brief Summary of the Invention

In accordance with the present invention, cell culture apparatus for the growth of cells in vitro is provided which employs elongate, selectively permeable hollow fibers in a shallow layer configuration as a matrix for cell attachment on the outer surface of the fibers, and aeration of the cells by passage through the interior of said fibers and permeation of the membrane wall. The flow path of the culture media is directed by distributor plate means substantially uniformly through the fiber layer and substantially normal or transverse to the plane of the elongate axes of the fibers. A relatively shallow bed of fibers and a relatively short path of media flow are thus employed whereby the gradient of nutrients and metabolic products is substantially reduced from that produced by the bundle or cartridge configuration of the prior art and a more extensive utilization of fiber surface is obtained. By the term shallow layer is meant a layer or bed in which the length and width are substantially greater than the distance therebetween or thickness of the layer.

Detailed Description of the Invention

In the present invention, several variations of the cell culture apparatus are contemplated by the inventors. While the specification concludes with claims particularly pointing out and distinctly claiming the subject matter regarded as forming the present invention, it is believed that the invention and its advantages will be better understood from the following description of the preferred embodiments taken in connection with the accompanying drawings in which:

Figure 1:
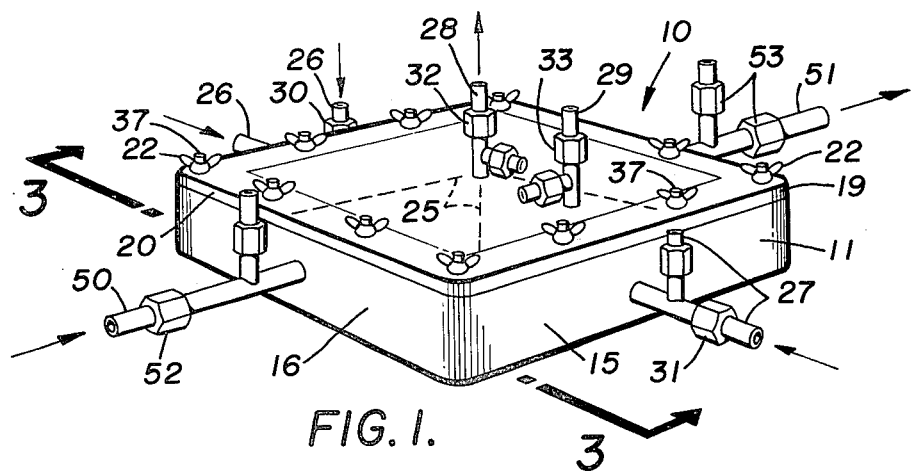
FIG. 1 is a perspective of one embodiment of the cell culture apparatus of the invention.
Figure 2:
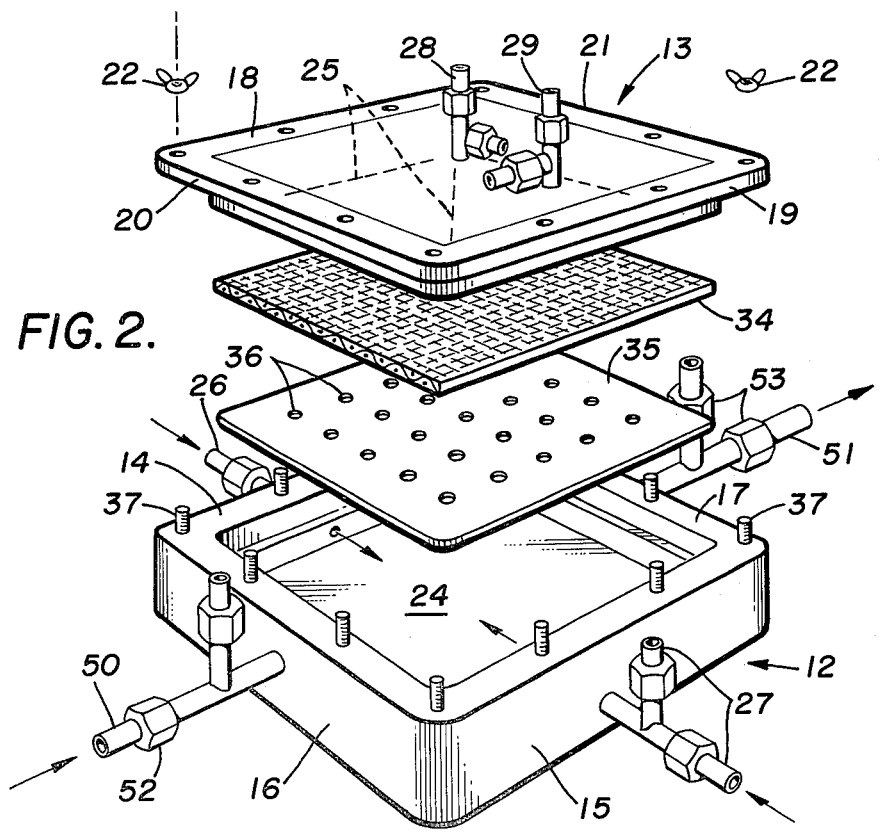
FIG. 2 is an exploded view of the apparatus of FIG. 1 showing internal parts.
Figure 3:
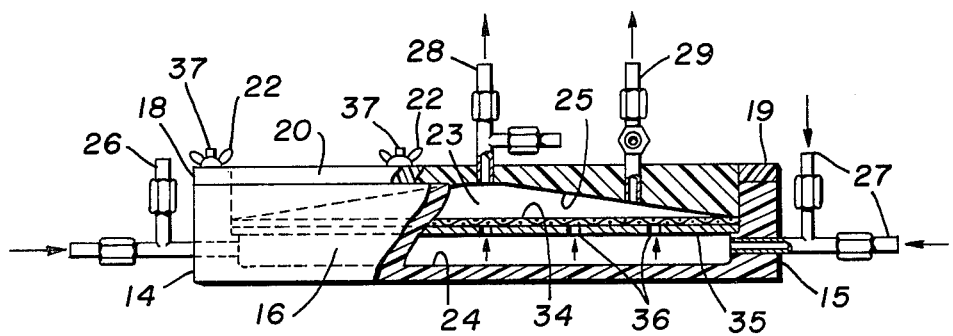
FIG. 3 is an end view taken along the line 3—3 of FIG. 1 showing assembled features partly in section.

Turning now to FIGS. 1 to 3 of the drawings, reference numeral 10 refers generally to a cell culture reactor. Reactor 10 is comprised of a generally rectangular parallelipiped housing 11 having separable lower part 12 and upper part 13. Lower housing part 12 has parallel sidewalls 14 and 15 and parallel endwalls 16 and 17. Similarly, upper housing part 13 has parallel sidewalls 18 and 19 and parallel endwalls 20 and 21. In upper housing part 13, the lower portions of walls 18, 19, 20 and 21 are recessed to fit snugly within the confines of the inner sides of walls 14, 15, 16 and 17, respectively, of lower housing part 12, while the upper flanged portions of walls 18, 19, 20 and 21 are adapted to seat flush on the upper rim of walls 14, 15, 16 and 17.

The two parts of housing 11 are suitably secured together with conventional fastener means such as bolts 37 with wing nuts 22 as illustrated, or with clamps, screws, and the like means. An adhesive closure means for the two housing parts also can be employed, if desired.

In the closed position, parts 12 and 13 define a chamber 23 within the housing. The bottom wall 24 of the housing is essentially flat; whereas, the top wall 25 of the housing, as illustrated, has a generally conical shape whereby chamber 23 decreases in depth in all directions as it radiates from the center of top wall 25.

Disposed in the walls of reactor 10 and communicating with chamber 23 are media inlet ports 26 and 27 in the bottom part of housing 11, and media outlet port 28 in the center of the top part of the housing. The media inlet ports also communicate with a media supply source and pumping or gravity feeding means (not shown) while the media oulet port also communicates with a spent media collection vessel (not shown). An access port 29, which can be used for inoculation and sampling, also is disposed within the top part of housing 11. Each of ports 26, 27, 28 and 29 have adapters 30, 31, 32 and 33, respectively, which can be used for regulation of the media flow and the distribution of media into the cell reactor. The direction of flow through the media inlet and outlet ports is indicated by arrows.

A layer of elongate hollow fibers 34 is arranged in a relatively shallow, flat bed configuration within chamber 23 and supported by a rectangular distributor plate 35. A plurality of small openings 36 are substantially equidistantly spaced apart on the surface of plate 35 for upward passage of media. These openings or perforations can be, for example, from about one to about ten millimeters in diameter and can be conveniently spaced apart, for example, up to about ten centimeters apart. Plate 35 is suitably mounted within chamber 23 such that it lies in a substantially horizontal plane above the media inlets 26 and 27. Such mounting can be provided by conventional support means such as brackets, flanges, adhesive sealing and the like means. This distributor plate means effectively permits all the cells to be uniformly contacted with essentially the same fresh media without the formation of a media gradient.

The elongate fibers which are used for cell attachment in the cell culture reactor 10 are hollow tubes ranging generally from about 100 to about 1000 microns in diameter. These fibers can be produced from any suitable material which is non-toxic to the cells and can be appropriately spun into fibers, and which is permeable to gas and permits cell attachment thereto. The hollow fibers should be permeable to air and oxygen but impermeable to cells, and should have a Loeb structure which comprises an anisotropic thin layer or skin on top of a thicker layer having an open cellular structure. Suitable materials of construction include, for exaample, various acrylonitrile polymers, styrene polymers, polyionic polymers, polycarbonates, polysulfones, polycarbohydrates such as cellulose and cellulose derivatives, for example, cellulose acetate, triacetate and propionate esters, polypeptides such as collagen, fluorocarbons (for example, Du Pont Teflon), and the like synthetic resins. Examples of suitable hollow fibers made from these materials and methods of their production are disclosed in U.S. Pat. Nos. 3,228,876; 3,583,907; 3,691,068; 3,821,087; 3,883,393; 3,997,396; and 4,024,020.

The hollow fibers can be disposed in a parallel manner as shown in FIG. 2 or can be arranged, for example, in an ordered or randomly distributed mesh form so long as they have open ends for aeration through the interior of the fibers by suitable aeration means. The fiber bed also can comprise several thicknesses of individual fibers superimposed one upon the other, and generally use of from about one to about 50 such thicknesses of fibers is suitable. Separate layers of fibers can be interspersed with support plates or spacers, if desired. These support plates or spacers can be similar to distributor plate 35 or can be screens and the like means which allow passage of the culture media.

The fiber bed preferably has a generally square horizontal cross section to facilitate uniform distribution of culture media in all directions.

In an illustratibe example of a bed of fibers for a square reactor having bed dimensions of 10 cm×10 cm., about 300 fibers each having a diameter of $3.4 \times 10^{-2}$ cm. ideally can be placed side-by-side in one layer. A reactor with five such fiber layers will then have an effective fiber surface for cell attachment of about 1600 cm$^2$.

It will be appreciated that the cell culture reactor of this invention is not limited to the foregoing specific dimensions as other configurations will be apparent from the disclosure herein.

In order to provide suitable aeration, the reactor is provided with gas inlet and outlet conduit means for communicating with the interior of the holow fibers. Thus, oppositely disposed gas inlet port 50 and gas outlet port 51 are provided in the housing endwalls 16 and 17, respectively. Gas inlet port 50 permits the entry of air or oxygen through a header in endwall 16 and thence into the open ends of the hollow fibers embedded therein, and gas outlet port 51 permits the removal of exhaust gas from the other ends of the fibers similarly embedded in a header in endwall 17. Adapters 52 and 53 facilitate control of the flow of air or oxygen through the cell culture reactor. The direction of flow through the gas inlet and outlet ports is indicated by arrows. Air or oxygen can be readily pumped into the apparatus by a peristaltic pump (not shown) or other such pumping means.

In operation of an illustrative reactor, cell culture medium is fed into chamber 23 through inlet ports 26 and 27. The medium is inoculated through port 29 with a seed culture of suitable animal cells and the culture incubated at a temperature of from about 20° C. to about 40° C., preferably at about 35°-37° C. The cells which attach to the outer surface of the hollow fibers are aerated by passage of air or oxygen through gas inlet 50 and then distributed through the interior of the hollow fibers and allowed to permeate the fiber membrane wall. Exahust gas is expelled through gas outlet 51. During the incubation, periodic changes of media can be made, with the spent medium being expelled through outlet port 28 and fresh medium again being supplied through inlet ports 26 and 27. If desired, the culture medium can be aerated by conventional means prior to its being fed into the cell culture reactor. Following incubation, the desired metabolites or by-products of the cell growth can be isolated from the spent medium. Samples of macromolecular materials can be withdrawn through access port 29 at any desired time during the incubation. The reactor preferably is operated continuously whereby inlet ports 26 and 27 and outlet port 28 are kept in an open position and adjusted to any desired rate of flow of culture medium by suitable pumping or gravity feeding means. Similarly, gas inlet port 50 and gas outlet port 51 are kept open and adjusted to any desired rate of aeration by suitable pumping means.

The culture medium flows into the lower part of chamber 23 beneath perforated plate 35 which thereby serves as manifold or distributor means to provide uniform distribution of the medium and a flow path which is upward and transverse to the plane of the elongate axes of the fibers. The reduction of the depth of the upper part of chamber 23 in a manner dependent upon its distance from the media outlet 28 assists in the uniform collection of the spent media across the top of the bed of fibers in a manner which corresponds to the demand for the media passing across the fibers, thereby resulting in improved uniformity of flow throughout the chamber.

The combination of the flow path which is transverse to the bed of fibers and the relatively short length of flow through the fiber bed provides a more uniform culture media flow than obtained otherwise with parallel flow through a bundle of capillaries as employed in the prior art. It also promotes a more even distribution of cell growth on the fibers and greater utilization of the available fiber surface. The configuration of the reactor of this invention thereby overcomes the deficiencies in the prior art parallel flow reactors in which cells cannot adequately penetrate the fiber bundle and in which nutrients are utilized at the inlet end with gradual nutrient depletion and undesirable metabolite production as the media flow reaches the distal end of the reactor.

It should be understood that all types of animal cells can be cultured in the apparatus of this invention such as, for example, mammalian, amphibian and avian cells. Typical examples are human lung fibroblast (WI-38), rhesus monkey kidney (MK-2), cervical carcinoma (HeLa), chick fibroblast, simian virus 40 transformed 3T3 mouse embryo fibroblast (SV3T3) and baby hamster kidney (BHK) (ATCC No. CCL 10) cells. So also, the apparatus is adapted for use with any conventional culture media such as Eagle's basal medium, Dulbecco's modified Minimum Essential Medium (MEM) and Earle's or Hank's balanced salt solutions fortified with appropriate nutrients, fetal calf sera, and the like materials.

Figure 4:
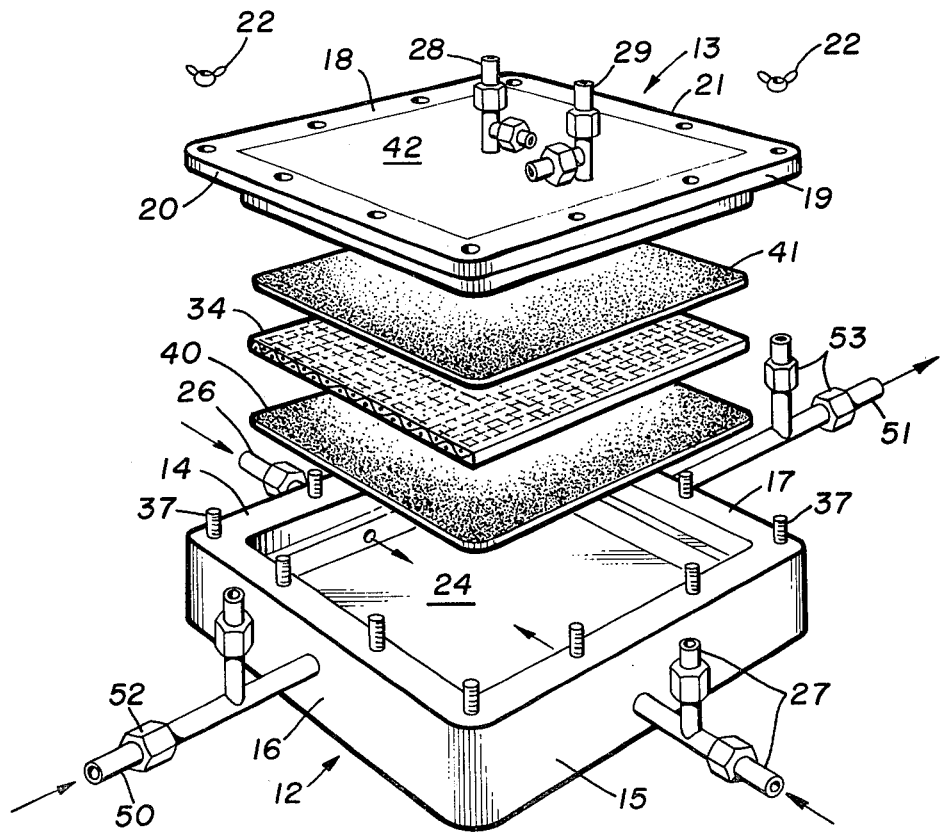
FIG. 4 is an exploded view of another embodiment of the invention.

Referring now to FIG. 4, a modified cell culture reactor of this invention comprising lower and upper housing parts 12 and 13, respectively, is disclosed. Media inlets 26 and 27, media outlets 28, gas inlet 50 and gas outlet 51 are essentially the same as in FIGS. 1 to 3, as is access port 29 and the layer of fibers 34. However, a microporous filter plate 40 has been substituted for the perforated distributor plate 35 of FIGS. 1 to 3. The microporous filter plate can be made of, for example, stainless steel or silver, and preferably has a pore size ranging from about 0.5 to about 10 microns. It advantageously provides a still more even distribution of culture media than provided by distributor plate 35. The fiber bed also can be sandwiched between a pair of microporous filters, in which case the lower filter 40 serves as the distributor plate means while the upper filter 41 serves a a diffusion barrier to prevent cells from passing through the outlet port and to stop back-flow of spent media. The upper filter preferably has a pore size ranging from about 10 to about 100 microns. In the latter embodiment, the access port 29 should be located below the horizontal plane of the upper filter, and the top 42 of the reactor preferably will be flat rather than concave as shown in FIGS. 1-3.

The shallow bed cell culture reactor of this invention also lends itself to multiple unit configurations. For example, a plurality of the reactors can be readily shelved in an incubator to provide a cell culturing system with all the advantages described herein on a large scale basis.

Figure 5:
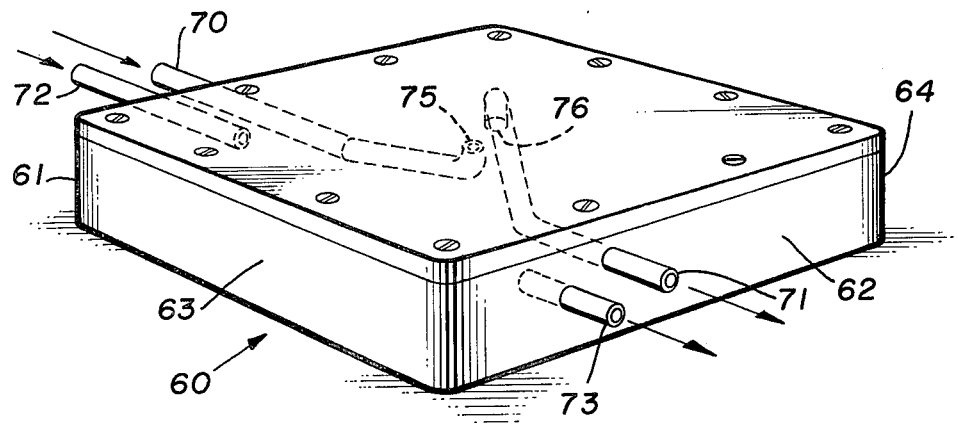
FIG. 5 is a perspective of yet another embodiment of the invention.
Figure 6:
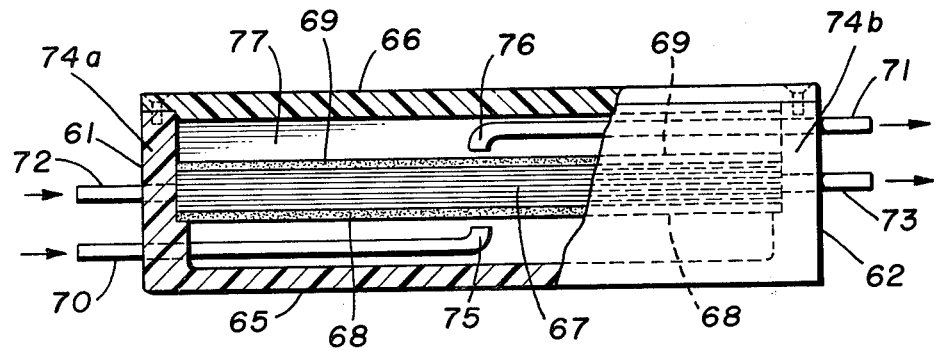
FIG. 6 is a front view of the apparatus of FIG. 5 taken partly in section.
Figure 7:
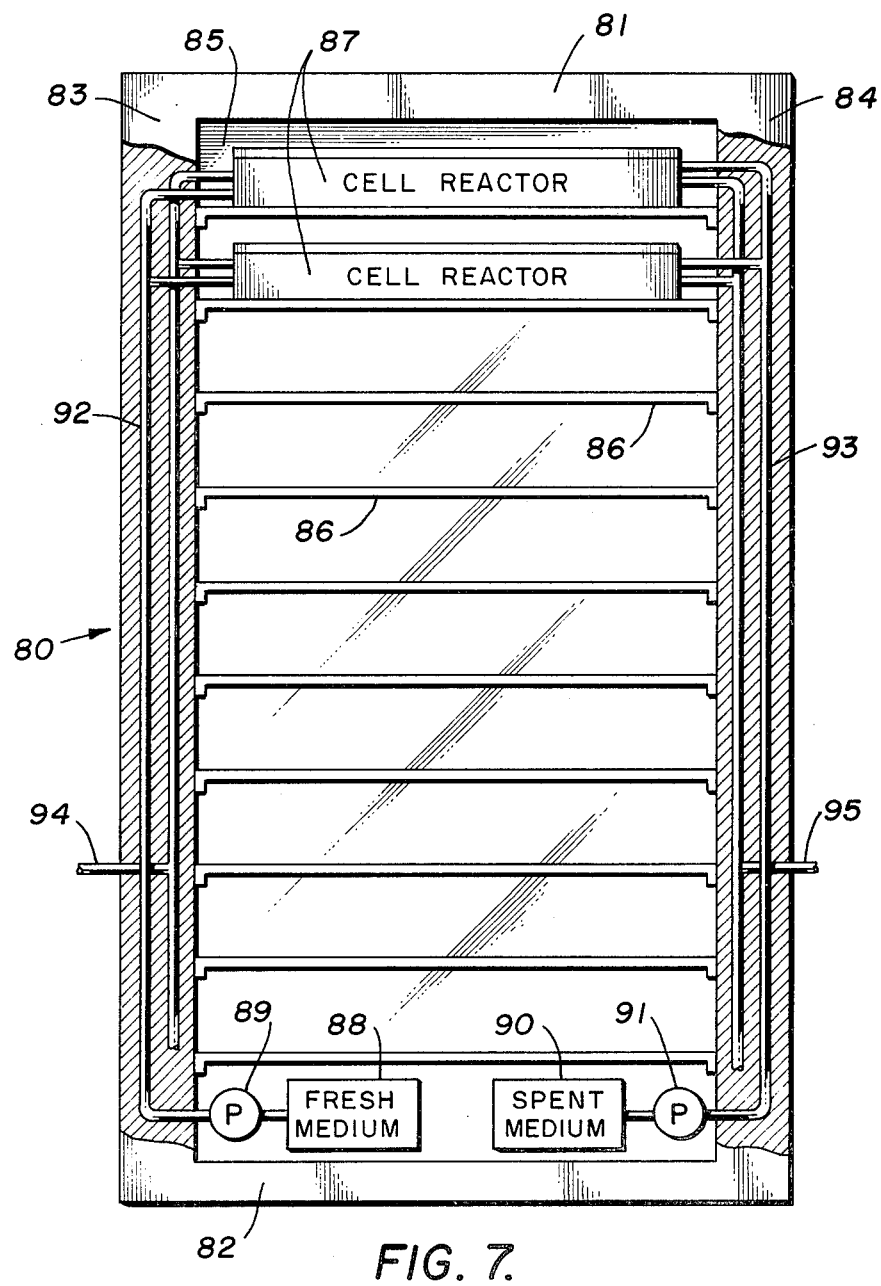
FIG. 7 is a front diagrammatic view of a multiple unit module embodiment of the invention.

FIGS. 5 to 7 illustrate one such multiple unit embodiment of the invention. In particular, FIGS. 5 and 6 show a cell culture reactor 60 adapted for use in the cell culture reactor module 80 of FIG. 7. The cell culture reactor has sidewalls 61 and 62, front wall 63, rear wall 64, bottom wall 65 and top wall 66. The upper part of the reactor is shown to be fastened to the lower part of the reactor with countersunk screws placed around the periphery at the top wall. A bed of elongate hollow fibers 67 is arranged in a shallow layer sandwiched between a lower microporous filter plate 68 and an upper microporous filter plate 69 in reactor chamber 77.

Culture medium inlet tube 70 and gas inlet tube 72 lead into the reactor chamber 77 through sidewall 61 while culture medium outlet tube 71 and gas outlet tube 73 correspondingly exit from the reactor chamber through sidewall 62. The direction of flow through these tubes is indicated by arrows.

Gas which enters through inlet tube 72 is distributed to the open ends of the elongate hollow fibers in the sidewall at 74a and then flows through the interior of the hollow fibers. Exhaust gas is collected at the other sidewall at 74b and then removed from the cell culture reactor through outlet tube 73. Reference numerals 74a and 74b represent headers whereby the gas inlet and oulet tubes communicate with the interior of the hollow fibers.

The culture medium which enters through inlet tube 70 is shown to be directed into the lower portion of chamber 77 at opening 75 for entry at a point beneath about the center of lower microporous plate 68. Culture medium which flows upwardly through the bed of hollow fibers sandwiched between the two microporous filter plates and into the upper portion of chamber 77 is collected at opening 76 above a point at about the center of upper microporous filter plate 69 and then exits through aoutlet 71. The inlet and outlet tubes can be angled as shown in FIG. 5 to provide these centrally located openings.

Now with particular reference to FIG. 7, a cell culture reactor module is indicated generally by reference numeral 80. This module can be in the nature of an incubator or a similar such receptacle having shelves for placement of a plurality of cell culture reactors of the general configuration illustrated in FIGS. 5 and 6. A front diagrammatic view of such a receptacle is shown in FIG. 7. In this view, the front door is removed and portions of the side panels 83 and 84 to which the door can be affixed are broken away in order to show the inside structure of the reactor module. Upper panel 81 and lower panel 32 are also shown in the front view of FIG. 7. The module chamber 85 is shown to have ten shelves 86, each of which accommodates one cell culture reactor 87 of the type shown in FIGS. 5 and 6. For the sake of simplicity, only two such reactors are illustrated.

The cell culture reactors are supplied with fresh medium from reservoir 88 by means of a pump 89. Spent medium is withdrawn from the cell reactors into a collection reservoir 90 by means of a pump 91. The fresh medium inlet tubing 92 is suitably branched to supply each of the two illustrative cell culture reactors 87. Corresponding branches in the outlet tubing 93 are shown for withdrawing spent medium from each cell culture reactor. Similar such tubing branches can be provided for cell culture reactors placed on the other shelves of the module.

In a like manner, branches in gas inlet tubing 94 lead to each reactor and branches in gas outlet tubing 95 lead away from each reactor to provide appropriate aeration of the reactor chamber with air or oxygen.

In the illustrative module shown in FIG. 7, all the reactor controls and conduit can be readily accessible to the operator from the front opening of the module in a convenient and compact arrangement by use of appropriate plug-ins and connector means. For example, the inlet and outlet tubing can be placed close to the front wall of the reactor as seen from FIG. 5.

In a typical example of a multiple unit configuration, a cell culture reactor module which utilizes a floor space of only about 4 feet by 4 feet and which has a height of only about 3 feet can readily accommodate ten reactors, each being about 40 inches×40 inches×2 inches high. When each such reactor is provided with a hollow fiber bed having an effective surface area for cell attachment of about 100 square feet, the total capacity of the module is about 1000 square feet. This is equivalent to 14 conventional cell culture roller bottle stacks having from 90 to 100 bottles per stack and about 0.6 to 0.7 square foot of surface per bottle. The savings in time, space and manpower required for operating the cell culture reactor module of this invention as compared to conventional roller bottle operation is thus readily apparent from the foregoing disclosure.

It will be appreciated that many other modifications and variations can be made to the particular embodiments of the invention described hereinbefore without departing from the basic and novel concepts of the invention. For example, other ports such as overflow ports or additional access and feed ports can be provided in the reactor at various convenient locations in the reactor walls. In the embodiments having a plurality of fiber layers, suitable spacers can be employed to impart any desired spaced-apart relationship between the respective layers. The separable upper and lower housing parts can have other suitable shoulder means to provide fluid-tight engagement of the parts. The open ends of the fibers can be secured in a removable header with potting means such as epoxy and the like setable organic cement materials which can act as a sealant for the fibers. The media inlet ports can additionally have small openings circumferentially spaced about a tubular conduit leading into the reactor chamber to provide a radial dispersion of the fresh culture media.

The materials of construction of the reactor can be metal or plastic materials which lend themselves to fabrication of a relatively rigid structure. Injection molded plastic parts and fabricated metal parts generally can be used for the reactor. Use of clear plastic materials such as, for example, polycarbonate, polystyrene and methyl acrylate plastics, are preferred when it is desired to facilitate visual observation of the cell growth. Use of stainless steel is preferred for its adaptability to steam sterilization. In general, biologically inert materials should be used for fabrication of any parts of the reactor which will come into contact with the culture media and the growth products.

Various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A cell culture reactor comprising: a housing, a reaction chamber within said housing, external culture medium inlet and outlet means disposed in walls in said housing and in fluid communication with said chamber, a plurality of elongate, selectively permeable, open ended hollow fibers arranged in a shallow layer within said chamber whereby the open ends of said fibers lead to external inlet and outlet gas means disposed in walls in said housing and in gaseous communication with the interior of said hollow fibers, and microporous distributor plate means adapted to provide a substantially uniform culture medium flow path substantially transverse to the plane of the elongate axes of said fibers, said hollow fibers being permeable to air and oxygen and said microporous distributor plate means being positioned substantially parallel to said fiber layer and between said fiber layer and said medium inlet means.

2. The cell culture reactor of claim 1 in which the microporous distributor plate means is a microporous filter plate.

3. The cell culture reactor of claim 2 in which an outlet microporous filter is positioned on the outlet side of and substantially parallel to said fiber layer.

4. The cell culture reactor of claim 3 in which the inlet microporous filter distributor plate has a pore size of from about 0.5 to about 10 microns and the outlet microporous filter has a pore size of from about 10 to about 100 microns.

5. The cell culture reactor of claim 1 including access port means communicating with said chamber for inoculation and sampling.

6. The cell culture reactor of claim 1 in which the housing has a tapered top wall whereby said chamber decreases in depth in all directions as it radiates from the center of said top wall and in which the culture medium outlet means is positioned in the center of said top wall.

7. The cell culture reactor of claim 1 in which said housing comprises separable upper and lower parts with recessed shoulder means on one of said housing parts adapted for fluid-tight engagement with the inner walls of said other housing part.

8. The cell culture reactor of claim 1 in which the fiber layer comprises from about one to about 50 thicknesses of individual fibers.

9. The cell culture reactor of claim 1 in which said housing comprises separable upper and lower parts with recessed shoulder means on one of said housing parts adapted for fluid-tight engagement with the inner walls of said other housing part and in which the fiber layer is sandwiched between an upper microporous filter having a pore size of from about 10 to about 100 microns and a lower microporous filter plate as the distributor plate means and having a pore size of from about 0.5 to about 10 microns.

10. A cell culture reactor module comprising, a hollow receptacle for incubation containing parallel shelves capable of supporting cell culture reactors in a spaced-apart manner, a plurality of vertically stacked and spaced-apart cell culture reactors disposed on said shelves within said hollow receptacle for incubation, each said reactor comprising: a housing, a reaction chamber within said housing, external culture medium inlet and outlet means disposed in walls in said housing and in fluid communication with said chamber, a plurality of elongate, selectively permeable, open ended hollow fibers arranged in a shallow layer within said chamber whereby the open ends of said fibers lead to external inlet and outlet gas means disposed in walls in said housing and in gaseous communication with the interior of said hollow fibers, and microporous distributor plate means adapted to provide a substantially uniform culture medium flow path substantially transverse to the plane of the elongate axes of said fibers, said hollow fibers being permeable to air and oxygen and said microporous distributor plate means being positioned substantially parallel to said fiber layer and between said fiber layer and said medium inlet means, common culture medium inlet and outlet means contained in a wall of said hollow receptical which provide fluid communication with each respective common culture medium inlet and outlet means in each of said cell culture reactors and a common gas inlet and outlet means contained in a wall of said hollow recepticle which provide gaseous communication with each respective common gas inlet and outlet means in each of said cell culture reactors.

* * * * *

UNITED STATES PATENT AND TRADEMARK OFFICE
CERTIFICATE OF CORRECTION

PATENT NO. : 4,201,845
DATED : May 6, 1980
INVENTOR(S) : Joseph Feder, Katharine Ku, Mau-Jung Kuo It is certified that error appears in the above-identified patent and that said Letters Patent are hereby corrected as shown below:

In the title page, the third inventor's name, Mau-Jung Ku" should read --Mau-Jung Kuo--. In the Abstract, line 7, "cell" should read --wall--. In Columns 3-4, lines 68 and 1, "exaample" should read --example--. Column 4, line 28, "illustratibe" should read --illustrative--. Column 6, line 55, "aoutlet" should read --outlet--. Column 10, line 9, "receptical" should read --receptacle--. Column 10, line 13, "recepticle" should read --receptacle--.

Signed and Sealed this

Fifteenth Day of July 1980

[SEAL]

Attest:

SIDNEY A. DIAMOND

Attesting Officer  Commissioner of Patents and Trademarks